(12) United States Patent
Utterberg

(10) Patent No.: US 6,196,519 B1
(45) Date of Patent: Mar. 6, 2001

(54) SQUEEZE CLAMP FOR FLEXIBLE TUBING

(75) Inventor: David S. Utterberg, Seattle, WA (US)

(73) Assignee: DSU Medical Corporation, Las Vegas, NV (US)

( * ) Notice: Subject to any disclaimer, the term of this patent is extended or adjusted under 35 U.S.C. 154(b) by 0 days.

(21) Appl. No.: 09/396,837

(22) Filed: Sep. 15, 1999

Related U.S. Application Data

(62) Division of application No. 08/943,672, filed on Oct. 3, 1997.

(51) Int. Cl.[7] .................................................. F16K 7/04
(52) U.S. Cl. .................................................. 251/10; 251/9
(58) Field of Search ......................... 251/10, 9, 4

(56) References Cited

U.S. PATENT DOCUMENTS

| | | |
|---|---|---|
| 3,204,636 | 9/1965 | Kariher et al. . |
| 3,419,245 * | 12/1968 | Scola ..................... 251/10 |
| 3,713,622 | 1/1973 | Dinger . |
| 3,942,228 | 3/1976 | Buckman et al. . |
| 4,053,135 * | 10/1977 | Saliaris .................. 251/10 |
| 4,235,412 * | 11/1980 | Rath et al. .............. 251/10 |
| 4,266,751 | 5/1981 | Akhavi . |
| 4,589,626 * | 5/1986 | Kurtz et al. ............ 251/10 |
| 4,643,389 * | 2/1987 | Elson et al. ............ 251/10 |
| 4,673,161 * | 6/1987 | Flynn et al. ............ 251/10 |
| 4,802,650 * | 2/1989 | Stricker ............. 251/10 X |
| 5,035,399 * | 7/1991 | Rantanen-Lee ...... 251/4 X |
| 5,318,546 * | 6/1994 | Bierman ............ 251/10 X |

* cited by examiner

*Primary Examiner*—Kevin Shaver
*Assistant Examiner*—John Bastianelli
(74) *Attorney, Agent, or Firm*—Garrettson Ellis; Seyfarth Shaw

(57) ABSTRACT

A molded squeeze clamp for tubing which comprises a strip of plastic having first and second ends, the strip being bent back on itself so that the ends are adjacent to each other in the manner of a Halkey-Roberts clamp. The first strip end defines a first latch, for engagement and releasable locking with the second end, and the second end defines a second latch for locking with the first latch. The first end also defines a first projection extending towards the second end to reduce or eliminate a gap between the first and second ends when the clamp is in its unstressed, as-molded, open configuration. The second end defines a second projection to facilitate manual opening of the clamp, the second projection extending in substantially longitudinal relation to the axis of tubing carried in the squeeze clamp.

6 Claims, 1 Drawing Sheet

SQUEEZE CLAMP FOR FLEXIBLE TUBING

CROSS REFERENCE TO RELATED APPLICATION

This application is a division of application Ser. No. 08/943,672, filed Oct. 3, 1997, a continued prosecution application of the same serial number being filed on Feb. 15, 1999.

BACKGROUND OF THE INVENTION

The Halkey-Roberts clamp is a well-known type of one-piece plastic clamp which is used to close off plastic tubing such as polyvinyl chloride tubing.

While the clamp is in widespread use, certain technical disadvantages are found in the present designs of the clamp. The present clamps comprise a single strip of plastic in which the respective ends are curved towards each other to engage together in a snap-fit, spring relation in which a projection or pair of projections squeezes the tubing shut when the ends of the clamp are snapped together. The tubing can be opened by the separation of the projections when the ends of the clamps are separated.

It is desirable for the clamp in its as-molded, unstressed condition to have ends that are close together so that when large containers of the loose clamps are moved or shaken, the clamps do not hook together by random shaking and movement. At the same time, when this has been done, the tube-squeezing portions of the clamp tend to be close enough together to partially compress tubing placed through the clamp which, over a long period of time, can cause a crease or cleft to develop. This can particularly happen with polyvinyl chloride tubing. This crease can serve as a place where a kink in the tubing can develop during use, which is very undesirable.

As a further disadvantage of current designs of the Halkey-Roberts clamp, as one squeezes the ends of the clamp together to close it into a snap-fit, closed retention, the end of the clamp which carries a retention hook to engage the other end also carries an upstanding flange to facilitate re-opening of the clamp. Persons with long fingernails have substantial difficulty in closing the clamp because of this, while their fingers are pointed generally parallel to the axis of the clamp. Accordingly, such individuals close the clamp with their fingers placed transversely or sideways to the clamp. The effect of this often is to cause a skewing of the clamp ends as they close, leaving the clamp in a closed but twisted, undesirable configuration that may only partially close the tubing and thus permit leakage.

By this invention, an improved squeeze clamp is provided which eliminates the above disadvantages of the presently-used Halkey-Roberts clamp.

DESCRIPTION OF THE INVENTION

By this invention, a molded squeeze clamp for tubing is provided which comprises a strip of plastic having first and second ends. The strip is bent back on itself, typically having at least a pair of curved sections, so that the ends of the strip are adjacent to each other. The strip defines a pair of spaced apertures to permit a flexible tube to extend through the apertures, to thus be carried by the clamp.

At least one projecting portion is carried by one section of the plastic strip to project inwardly of the curved strip. The purpose of this projecting portion is to press closed and to seal the flexible plastic tube carried by the clamp, by pressing the tube against another section of the strip. An optional second projecting portion may squeeze the tube from the other side.

The first strip end defines a first latch for engagement and releasable locking with the second end. The first end also defines a first projection, which extends towards the second end to reduce or eliminate a gap between the first and second ends when the clamp is in its unstressed, as-molded, open configuration, which is the configuration that permits fluid flow through the tube carried by the clamp. Thus, the presence of the first projection basically eliminates the problem of hooking together of the clamps as discussed above, when the clamps are stored together in a container. The first projection, which may be an extending plate, spaced bars, or the like, closes or reduces the opening between the ends, so that one squeeze clamp does not pass through the respective ends of another squeeze clamp during shaking or other movement of a box of the clamps loosely lying together, thus avoiding the hooking-together problem.

The second end of the clamp defines a second latch for releasable engaging the first latch, when the clamp is in its tube-closing configuration.

Thus, a clamp is provided in which the tube-closing projecting portion may be more widely spaced in open position from the other section of the strip against which it presses to close the tubing, this spacing being of a desirable degree so that the tubing is not partially collapsed and creased through cold flow upon storage over a period of time by the projecting portion in open position. In the situation of the prior art clamps, the spacing between the respective clamp ends would be too great if the tube-closing projecting portion were sufficiently widely spaced from the other strip section. Thus, the prior art has either the serious problem of hooking together of the clamps upon bulk storage, or the serious problem of tube creasing.

By this invention, the presence of the first projection extending from the first end toward the second end keeps any space between the respective ends low or even non-existent, so that a clamp is provided which is free from the hooking-together problem, which can also be free from the problem of the creation of a cold flow crease in the flexible tubing that it carries upon lengthy storage. This cold flow problem is particularly found in polyvinyl chloride tubing.

The squeeze clamp of this invention may also carry a second projection on the second end, to receive a finger for clamp opening. This second projection extends outwardly from the end in a direction which is substantially longitudinal to the direction of extension of tubing carried in the clamp. Thus, the second projection is out of the way of the fingers of the user who is pressing the first end of the clamp into a locking relation with the second end. This means that people with long fingernails do not have to place their fingers laterally or in sideways manner to the clamp as they close the clamp. Thus, the undesirable skewing which may take place in that circumstance can be avoided.

To the contrary, the corresponding component of the main, commercial Halkey-Roberts clamp slopes at a substantial angle to the direction of tubing extension, and thus interferes with opening of the clamp by people with long fingernails.

The second projection is for the purpose of facilitating the manual movement of the second end of the clamp, to release the latch and cause the clamp to spring back to its open, unstressed configuration.

DESCRIPTION OF SPECIFIC EMBODIMENTS

Figure 1:
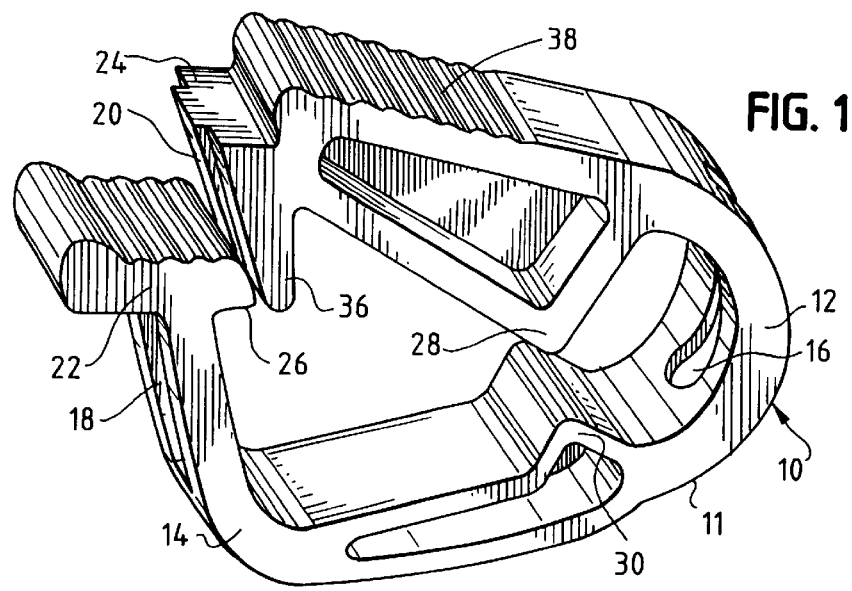
FIG. 1 is a perspective view of the molded squeeze clamp of this invention, shown in substantially its open, unstressed, as-molded configuration.

Referring to the drawings, squeeze clamp 10 is shown, being made of a strip of semi-flexible plastic, which is generally rigid except at flexible, curved portions 12, 14, which are rendered somewhat flexible by the presence of central apertures 16, 18, respectively placed in the curved portions 12, 14, and adjacent areas. Apertures 16, 18 are also for the purpose of receiving flexible tubing 21, which may be tubing of a fluid flow set such as a set for blood or medical solutions, and which extends through the apertures of the clamp as shown in FIGS. 2 and 3 in a manner that is generally conventional for a Halkey-Roberts squeeze clamp.

Clamp 10 is bent at sections 12, 14, so that the respective ends 20, 22, are adjacent to each other in closely spaced relation.

The plastic portion of the strip defining the first clamp end 20 also defines the first latch, which is embodied in latch hook or ledge 24, for engagement and releasable locking with the second clamp end 22. Second clamp end 22 defines a second latch 26, which, as shown in FIG. 2, comprises a second hook or ledge, so that the two latches 24, 26, can engage each other in the closed position of clamp 10, in which clamp 10 is tensioned and biased to spring back to the open, unstressed position of FIG. 1, when latches 24, 26, are released.

Figure 2:
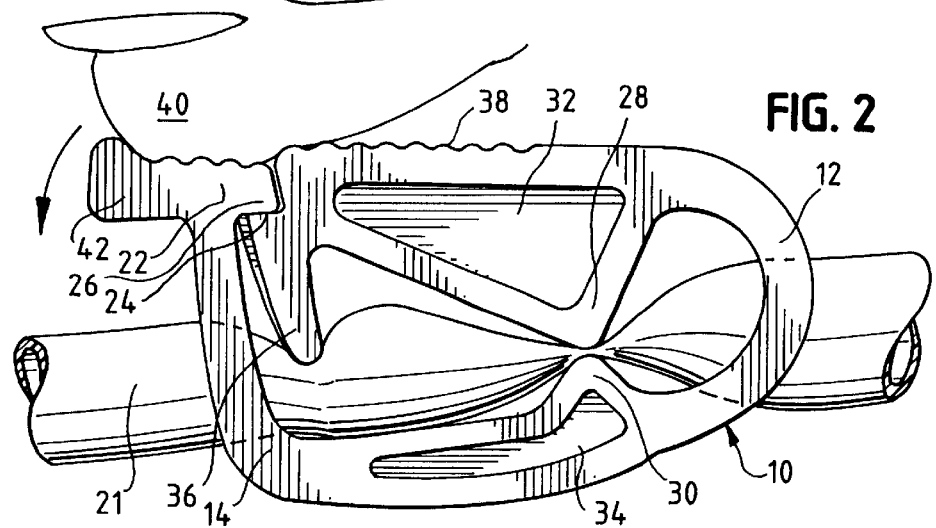
FIG. 2 is a perspective view of the molded squeeze clamp of FIG. 1, carrying flexible tubing which it seals, and shown in the closed position.
Figure 3:
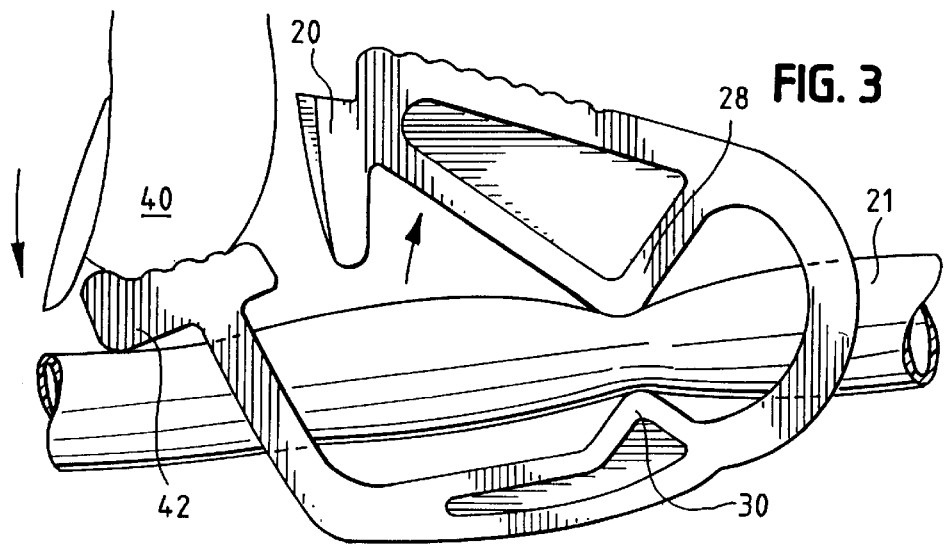
FIG. 3 is an elevational view showing how the clamp may be opened by manual outward movement of the second clamp end while manually pushing outwardly on the horizontal second projection, which is part of the second latch, to cause the clamp to spring open back toward its unstressed, as-molded configuration.

Plastic strip 11 of the clamp 10 also defines a pair of projecting portions 28, 30, which are positioned at separate regions of strip 11 to abut each other in the closed configuration of FIG. 2, and to squeeze tube 21 closed between them. It can be seen that the respective projecting portions 28, 30 are an integrally molded part of strip 11. Cut-out portions 32, 34, may be provided to reduce the amount of plastic in the clamp.

An inwardly extending first projection 36 is defined at first end 20 of the clamp. This projection 36 is shown to be an inwardly extending wall, but other configurations having a similar function may also be used as an alternative structure thereto. Basically, projection 36 is present to reduce or eliminate space between the first and second ends 20, 22 in the unstressed, open configuration of FIG. 1. In the absence of inwardly extending projection 36, there would be a substantial space between the respective ends 20, 22 of the clamp, which would allow the bulk stored clamps to interlink or hook together, which seriously interferes with their automated use in the manufacture of tube sets. Because of the presence of projecting portion 36, the hooking together or interlinking problem can be substantially eliminated, while the clamp 10 may have a substantial space between projections 28, 30 when open, wide enough to prevent any significant crimping of a tube 21 carried in the clamp, which crimping can cause creasing of the tube during storage prior to use of a set carrying the clamp of this invention.

If desired, projection 36 may be long enough to provide a second, auxiliary seal line for closing off tube 21 in the closed position of FIG. 2. Alternatively, if desired, first projection 36 may do double duty and function as the projecting portion which is carried by the one section of the strip, to provide the primary seal of tubing 21 when the clamp is closed. In that circumstance, projecting portion 28 might be eliminated, and projecting portion 30 might also be eliminated, or shifted to engage first projection 36 for better tube closure.

To close the clamp from the configuration of FIG. 1 to that of FIG. 2, upper end surface 38 of the clamp may be pushed with the finger downwardly to cause first end 20 to enter into a snap-locking relationship with the second end 22, as shown in FIG. 2, which closes off tube 21. To open the clamp again, finger 40 may be placed on the second, horizontal projection 42 at second end 22 of the clamp, pivoting second end 22 a bit to unlock the engagement between latch members 24, 26. First end 20 of the clamp then springs outwardly, which causes the separation of the respective sealing projecting portions 28, 30, and opening of the clamp.

Also this invention, second projection 42 extends in a direction which is generally longitudinal to the axis of the tubing 21 carried within the clamp. It is also shown to extend in a direction which is generally parallel to the plane generally defined by upper surface 38 of the clamp, near first end 20, when the upper surface is pressed to lock the clamp into the closed configuration of FIG. 2. Also, the projection's longitudinal extension is essentially not less that the height of the projection i.e. in its transverse dimension. This is contrary to the corresponding clamps of the prior art, where the projection corresponding to projection 42 occupies a substantial angle to the general axis of tube 21 carried in the clamp. Because of this angular relation of the corresponding structure of the prior art, those with long fingernails have had difficulty in closing prior art clamps into the locked FIG. 2 configuration, and have thus been forced to place their fingers sideways on surface 38 of the clamp to press the clamp down. Such closing from the side can cause the respective arms of the clamp to skew with respect to each other, causing a possible poor seal of tubing 21.

By this invention, persons with long fingernails can close this clamp while their respective fingers 40 are positioned longitudinally to the tube axis, which positioning makes a straight, unskewed lock of the clamp much more likely, along with a corresponding complete, good seal of tube 21.

The above has been offered for illustrative purposes and is not intended to limit the scope of the invention of this application, which is as defined in the claims below.

That which is claimed:

1. A squeeze clamp for tubing, which comprises: a strip of plastic having first and second ends, said strip being bent back on itself to define a pair of generally straight sections separated by a bent strip hinge portion so that said ends are adjacent to each other, and spaced from each other in the open position; said strip defining a pair of spaced apertures to permit a flexible tube to extend through and be carried by said clamp in a direction generally longitudinal of said sections of the strip, and at least one portion carried by one section of said strip to close and seal said flexible plastic tube carried by said clamp by pressing said tube against another section of said strip, said first strip end defining a first latch for engagement and releaseable locking with said second strip end, said second end defining a second latch for engagement with the first latch and carrying a projection to facilitate opening of the clamp, said projection extending outwardly from said second end in a direction substantially longitudinal of the direction of extension of tubing being carried in said clamp, in which said projection extends outwardly from said second end in a substantially longitudinal direction for a distance that is essentially not less than the height of the projection in its transverse dimension, whereby said projection is out of the way of the fingers of the user pressing the first end of the clamp into locking relationship with the second end.

2. The squeeze clamp of claim 1 in which said another section of said strip carries a second projecting portion positioned to engage and squeeze tubing that is being engaged and squeezed by the one portion of the script.

3. The squeeze clamp of claim 1 which is made of a single molded piece of plastic.

4. The squeeze clamp of claim 1 in which said at least one portion is a projecting portion to engage said flexible plastic tube passing through the squeeze clamp with a projecting transverse edge.

5. The squeeze clamp of claim 4 in which said another section of said strip carries a second projecting portion positioned to engage and squeeze tubing that is being engaged and squeezed by the one portion of the strip, said squeeze clamp being made of a single, molded piece of plastic.

6. The squeeze clamp of claim 5 in which said flexible plastic tube passing between said projecting portions is squeezed with projecting, transverse narrow edges of said projecting portions.

* * * * *

UNITED STATES PATENT AND TRADEMARK OFFICE
CERTIFICATE OF CORRECTION

PATENT NO.    : 6,196,519 B1
DATED         : March 6, 2001
INVENTOR(S)   : David S. Utterberg It is certified that error appears in the above-identified patent and that said Letters Patent is hereby corrected as shown below:

<u>Column 4,</u>
Line 25, "that" should be -- than --.

<u>Column 5,</u>
Line 8, "script" should be -- strip --.

Signed and Sealed this

Twenty-first Day of August, 2001

Attest:

*Nicholas P. Godici*

NICHOLAS P. GODICI
*Attesting Officer*    *Acting Director of the United States Patent and Trademark Office*